(12) United States Patent
Morton (10) Patent No.: US 9,895,488 B2
(45) Date of Patent: Feb. 20, 2018

(54) CONDUCTIVE CODING OF SYRINGE INFORMATION

(71) Applicant: BAYER MEDICAL CARE INC., Indianola, PA (US)

(72) Inventor: Richard C. Morton, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 207 days.

(21) Appl. No.: 14/751,621

(22) Filed: Jun. 26, 2015

(65) Prior Publication Data

US 2015/0374907 A1 Dec. 31, 2015

Related U.S. Application Data

(60) Provisional application No. 62/018,205, filed on Jun. 27, 2014.

(51) Int. Cl.
*A61M 5/145* (2006.01)
*A61M 5/00* (2006.01)

(52) U.S. Cl.
CPC ......... *A61M 5/14546* (2013.01); *A61M 5/007* (2013.01); *A61M 2205/60* (2013.01); *A61M 2205/6018* (2013.01); *A61M 2205/6027* (2013.01); *A61M 2205/6063* (2013.01)

(58) Field of Classification Search
CPC ...... A61M 5/14546; A61M 2205/6027; A61M 5/007; A61M 2205/60; A61M 2205/6018; A61M 2205/6063
See application file for complete search history.

(56) References Cited

U.S. PATENT DOCUMENTS

| | | | |
|---|---|---|---|
| 5,383,858 A | 1/1995 | Reilly et al. | |
| 5,460,609 A | 10/1995 | O'Donnell | |
| 5,573,515 A | 11/1996 | Wilson et al. | |
| 5,800,397 A | 9/1998 | Wilson et al. | |
| 6,322,535 B1 | 11/2001 | Hitchins et al. | |
| 6,652,489 B2 | 11/2003 | Trocki et al. | |
| 6,743,202 B2* | 6/2004 | Hirschman | A61M 5/14546 604/131 |
| 2003/0006209 A1* | 1/2003 | Stefen | A61M 5/172 215/386 |
| 2004/0064041 A1 | 4/2004 | Lazzaro et al. | |
| 2005/0113754 A1 | 5/2005 | Cowan et al. | |
| 2012/0123257 A1 | 5/2012 | Stokes, Jr. et al. | |

* cited by examiner

*Primary Examiner* — Kevin C Sirmons
*Assistant Examiner* — Amber Stiles
(74) *Attorney, Agent, or Firm* — Joseph L. Kent; David Schramm; James R. Stevenson (57) ABSTRACT

A system for identifying information regarding a syringe assembly used with a fluid injector includes at least one syringe assembly having a barrel extending from a distal end to an open proximal end, at least one indicator provided on at least a portion of an outer circumferential surface of the barrel, an injector having at least one syringe port adapted to receive the at least one syringe assembly, and at least one sensor provided on or within at least a portion of each syringe port. The at least one indicator may conduct electricity corresponding to information regarding the at least one syringe assembly, which is identified by the at least one sensor.

19 Claims, 6 Drawing Sheets

FIG. 5

CONDUCTIVE CODING OF SYRINGE INFORMATION

CROSS REFERENCE TO RELATED APPLICATION

This application claims the benefit of U.S. Provisional Patent Application No. 62/018,205, filed Jun. 27, 2014, the disclosure of which is incorporated in its entirety by reference.

BACKGROUND

Field of the Technology

The present disclosure relates generally to a system including at least one syringe for use with a powered fluid injector and, more specifically, to a syringe assembly including conductive coding for identifying information regarding the at least one syringe assembly.

Description of Related Art

In many medical procedures, such as drug delivery, it is desirable to inject various medical fluids, for example, gene therapy, cell and biological agent delivery, and delivery of therapeutic agents generally, into a patient. Likewise, numerous types of contrast media (often referred to simply as contrast) are injected into a patient for many diagnostic and therapeutic imaging procedures. For example, contrast media are used in diagnostic imaging procedures such as X-ray procedures (including, for example, angiography, venography, and urography), computed tomography (CT) scanning, magnetic resonance imaging (MRI), and ultrasonic imaging. Contrast media are also used during therapeutic imaging procedures, including, for example, angioplasty and other interventional radiological procedures.

In recent years, a number of injector-actuated syringes and powered injectors for pressurized injection of fluids, such as contrast media, have been developed. By way of example, in a typical angiographic procedure, the medical practitioner places a cardiac catheter into a vein or artery. The catheter is connected to either a manual or an automatic contrast injection mechanism. Alternatively, in CT and MRI imaging procedures, contrast may be injected into a patient's vasculature, for example through a needle or peripheral cannula. Such imaging agents may be accompanied by or followed by injection of a medical flushing fluid, such as saline. The automatic contrast injection mechanism typically includes at least one syringe assembly connected to a powered injector having, for example, at least one powered linear actuator. Typically, an operator enters settings into an electronic control system of the powered injector for a fixed volume of contrast and/or saline and a fixed rate of injection. In many systems, there is no interactive control between the operator and the powered injector, except to start or stop the injection. In these cases, the injector utilizes a programmed injection protocol to complete the procedure. A change in flow rate in such systems occurs by stopping the machine and resetting the injection parameters. Automation of angiographic procedures using powered injectors is discussed, for example, in U.S. Pat. Nos. 5,460,609, 5,573,515, and 5,800,397, incorporated herein by reference.

Generally, liquids being injected into a patient, such as X-ray and magnetic resonance contrast, are clear pharmaceuticals delivered to a patient during or just prior to a medical imaging procedure. The liquids may be provided in syringes of different sizes to accommodate different volumes of fluid that are required for different patients. Such contrasts can be detected by sophisticated imaging systems, but are difficult to detect with the human eye. Different contrasts have different properties, which make it difficult for a single or standard detector system to measure a property of the contrast. On the other hand, it is desirable that the contrast be clear to enable the user to check for air bubbles, particulates, or other impurities before injecting the fluid into the patient. These impurities could be solid particles or chemicals with an identifiable color. For example, if certain X-ray contrast media is stored improperly, free iodine can be released, causing the contrast to have a yellow tint. For the visualization of air bubbles, particles, or chemicals, the contrast only needs to be transparent, but may be colored.

It is often necessary for the medical practitioner to validate each syringe assembly connected to the automatic fluid injection mechanism prior to performing the injection. Validation may include confirming that the syringe assembly is genuine (e.g. to prevent counterfeiting, use of inferior or miss-fitting syringes that may result in improper mating between the syringe assembly and injector or may not have the required tolerances for a particular injection procedure, possibly resulting in malfunction during the procedure) and determining various characteristics of the syringe assembly and fluid contained therein. For example, the medical practitioner may verify that identifying information, such as the syringe dimensions (e.g. diameter, length, and fluid volume), and fluid contents are correct for the procedure being performed. In addition, the medical practitioner may be required to provide certain information about the syringe assembly, such as frictional characteristics between the plunger and syringe barrel, fluid viscosity, delivery rate, and the like (referred to hereinafter as "injection parameters") to the fluid injector to control piston force and acceleration to deliver fluid at a desired and controlled flow rate. Other important identifying information may include manufacturer, lot number, expiration date or shelf-life indicator, etc. Including the various desired identifying information may be difficult given the amount of available surface area and aesthetic reasons. For example, if the identifying information covers too much surface area on the syringe, it may impact the technician's ability to determine if the syringe has been properly filled.

In some systems, the fluid injector includes a sensor or reader located on the fluid injector for automatically reading a label or tag provided on the syringe when the syringe assembly is inserted in the injector. The label or tag contains certain information about the syringe assembly. The fluid injector uses the information extracted from the label or tag to validate the syringe assembly and to control the injection. Some existing syringe identification procedures require specific labels or tags that are applied to the syringe assembly subsequent to manufacturing the syringe assembly. In certain cases, the medical practitioner must rotate the syringe assembly until the sensor or reader on the fluid injector is properly aligned with the syringe identification feature, resulting in extended pre-injection manipulation and possible syringe misidentification. The at least one label or tag may include a plurality of label or tag. Each label or tag may correspond to different information regarding the syringe assembly.

Therefore, there is a continued need for a syringe assembly, injector, and/or injection system capable of identifying and validating the size/volume of the syringe assembly, the source of the provided syringe assembly, and the medical fluid solution provided in the syringe assembly prior to injection, wherein ease of use and/or amount of information contained in the identification feature is increased. The syringe assemblies, injectors, and systems set forth in the present disclosure are configured to address some or all of the above-identified problems.

SUMMARY OF THE DISCLOSURE

The present disclosure generally relates to syringe assemblies, injectors, injector assemblies, and assemblies and to methods of identifying information provided from a syringe assembly used in conjunction with the injector and/or injector assembly.

According to one aspect of the disclosure, a system for reading identifying information regarding a syringe used for injection with an injector, such as a powered injector, is provided. The system for identifying information regarding a syringe assembly used with a fluid injector may include at least one syringe assembly having a barrel extending from a distal end to an open proximal end, at least one indicator provided on at least a portion of an outer circumferential surface of the barrel, an injector having at least one syringe port adapted to receive the at least one syringe assembly, and at least one sensor provided on or within at least a portion of each syringe port. The at least one indicator may conduct electricity corresponding to information regarding the at least one syringe assembly, which is identified by the at least one sensor.

The at least one indicator may comprise at least one conductive ink. The information regarding the at least one syringe assembly may include at least one of a syringe assembly type, physical dimensions of the at least one syringe assembly, flow characteristics of fluid stored in the at least one syringe assembly, a type of fluid stored in the at least one syringe assembly, manufacturer of the at least one syringe assembly, lot number, date of manufacture of the at least one syringe assembly, expiration of use date of the at least one syringe assembly, and combinations thereof. The at least one sensor may include at least one conductive elastomeric pad that contacts the at least one indicator and a flex printed circuit board that interprets the information regarding the at least one syringe assembly. Upon contacting the at least one conductive elastomeric pad, the at least one indicator may conduct electricity from at least one first electrical contact to at least one second electrical contact that corresponds to the information regarding the at least one syringe assembly and that is interpreted by the flex printed circuit board. A computer accessory or processor may be in communication with the at least one sensor where the computer may have software programming to interpret or "decode" the identifying information associated with the at least one indicator. The at least one indicator may extend around an entire outer circumferential surface of the barrel. The at least one indicator may be formed as at least one strip, at least one geometric pattern, or combination thereof. The at least one indicator may be formed on the proximal end of the syringe barrel. The at least one sensor may extend around at least a portion of an entire circumferential surface of the at least one syringe port. The at least one sensor may include at least two sensors. The at least two sensors may be spaced apart from one another along at least one of a longitudinal axis and a lateral axis of the at least one syringe port. The at least one indicator may be detectable by the at least one sensor when the at least one syringe assembly is engaged within the at least one syringe port. The at least one indicator may include a plurality of indicators. Each indicator may correspond to different information regarding the at least one syringe assembly.

In another aspect of the disclosure, a syringe assembly is provided. The syringe assembly may include a barrel extending from a distal end to an open proximal end, and at least one indicator comprising at least one conductive ink provided on at least a portion of an outer circumferential surface of the barrel.

The at least one indicator may correspond to identifying information about the syringe assembly. The identifying information may include at least one of a syringe assembly type, physical dimensions of the syringe assembly, flow characteristics of fluid stored in the syringe assembly, a type of fluid stored in the syringe assembly, manufacturer of the at least one syringe assembly, lot number, date of manufacture of the at least one syringe assembly, expiration of use date of the at least one syringe assembly, and combinations thereof. The at least one indicator may extend around the entire outer circumferential surface of the barrel. The at least one indicator may be formed as at least one strip, at least one geometric pattern, or combination thereof. The at least one indicator may be provided on the proximal end of the barrel.

In another aspect of the disclosure, a method for reading identifying information regarding a syringe assembly provided within a fluid injector is provided. The method may include providing a syringe assembly having at least one indicator comprising at least one conductive ink provided on at least a portion of a barrel of the syringe assembly; inserting the syringe assembly into a syringe port of a fluid injector; contacting the at least one indicator against at least one sensor, thereby causing the at least one indicator to conduct electricity from at least one first electrical contact to at least one second electrical contact; and receiving identifying information regarding the syringe assembly based on the electricity conducted by the at least one indicator.

Further details and advantages of various aspects described in detail herein will become clear upon reviewing the following detailed description of the various aspects in conjunction with the accompanying figures.

DESCRIPTION OF THE DISCLOSURE

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and descriptions provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. The term "proximal" refers to the direction towards the injector assembly or device and away from the patient. The term "distal" refers to the outward direction extending away from the injector assembly or device and toward the patient. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structure, construction, and method of operation, and many advantages may be understood and appreciated.

Figure 1A:
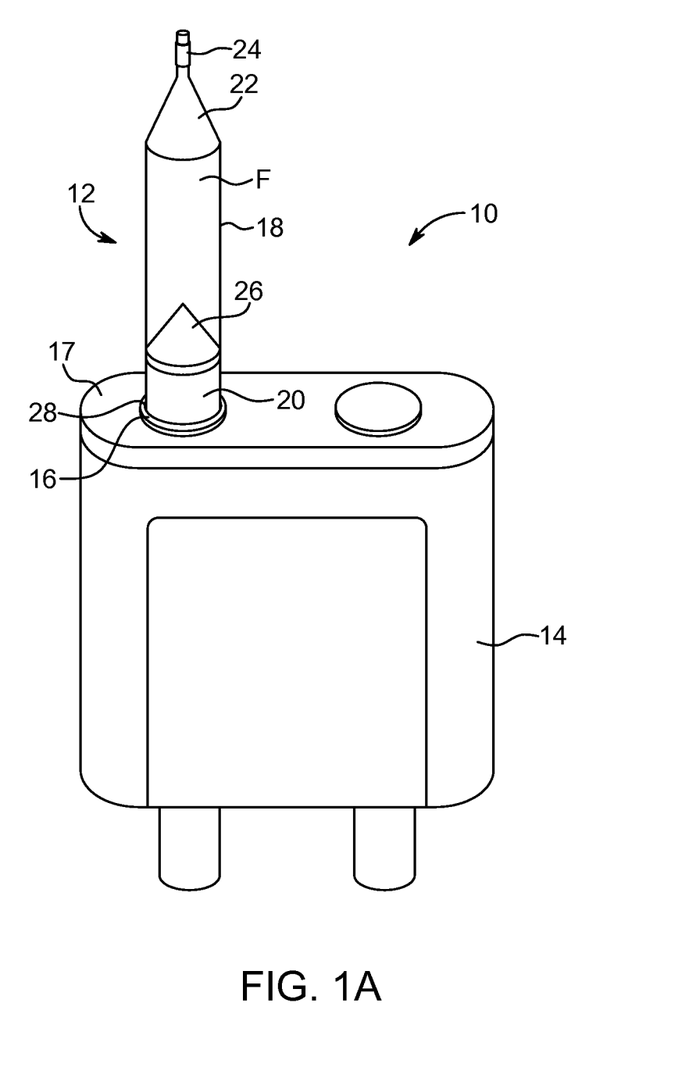
FIG. 1A is a perspective view of a fluid delivery system including a powered fluid injector and syringe according to an aspect of the disclosure.
Figure 1B:
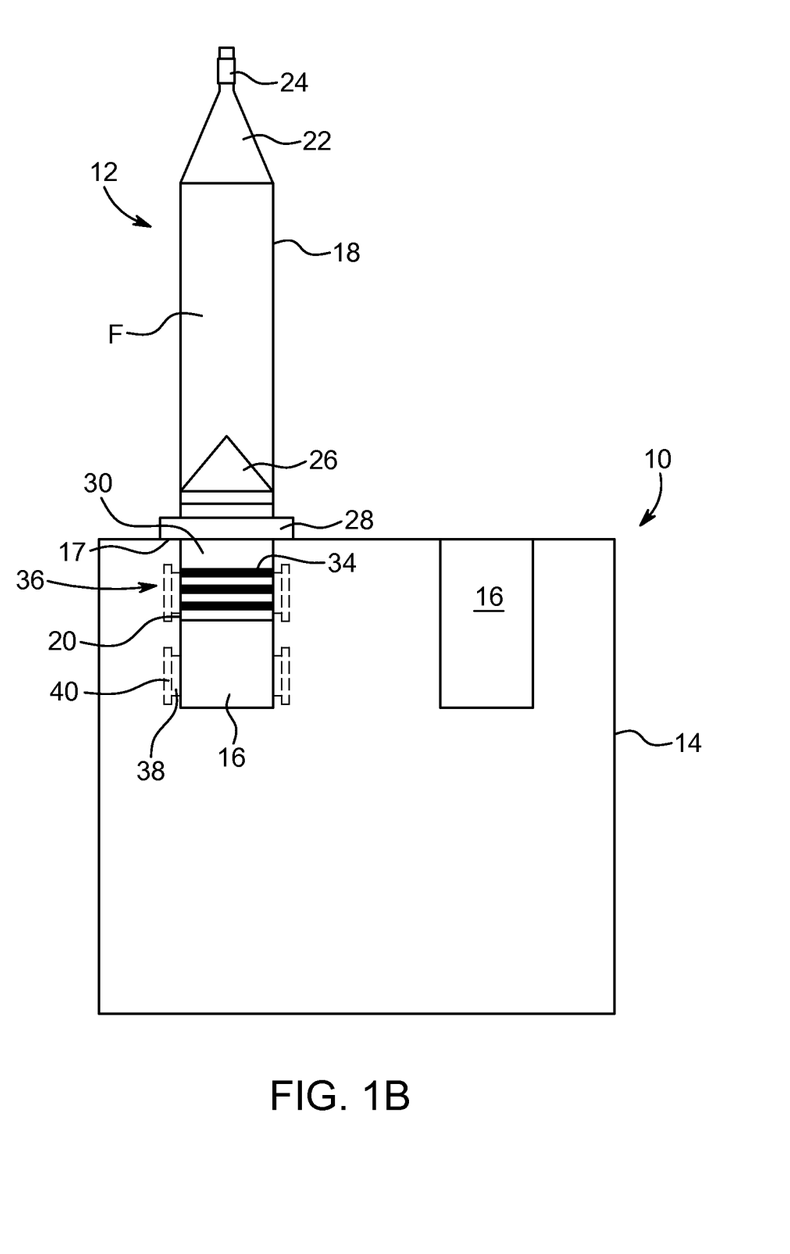
FIG. 1B is a cross-sectional view of the powered injector and syringe of FIG. 1A.

Provided herein are syringe assemblies, fluid injectors, and fluid delivery systems for injection of medical fluid, such as a medicament, a contrast agent, and/or saline, to a patient. The syringe assemblies, injectors, and fluid delivery systems are configured with various features to improve validation and identification of information regarding the syringe and/or the syringe contents prior to injection to a patient. With reference to FIGS. 1A and 1B, a fluid injector 10, such as an automated or powered fluid injector, is illustrated, which is adapted to interface with and actuate one or more syringe assemblies 12, which may be filled with a medical fluid F, such as contrast media, saline solution, or any desired medical fluid. The powered injector 10 may be used during an angiographic or computed tomography and like procedures to inject medicament, contrast agents, and/or conventional flushing agents, such as saline, into the body of a patient prior to, during, and/or after an imaging procedure. The powered injector 10 may be at least a dual-syringe injector, wherein the at least two fluid delivery syringe assemblies 12 are oriented in a side-by-side or other spatial relationship and are separately actuated by respective linear actuators or piston elements associated with the powered injector 10 to move a plunger 26 within the syringe body to aspirate or inject one or more fluids from the at least one syringe assembly 12. Other powered injectors may include a single syringe or three or more syringes. A suitable multi-syringe fluid injector is disclosed in U.S. Patent Application Publication No. 2012/0123257 to Stokes, Jr. et al., incorporated herein by reference.

The injector 10 may be enclosed within a housing 14 formed from a suitable structural material, such as plastic and/or metal. The housing 14 may be in various shapes and sizes depending on the desired application. For example, the injector 10 may be a free-standing structure configured to be placed on the floor or may be a smaller design for placement on a suitable table or support frame. The injector 10 includes one or more syringe ports 16 for reversibly interfacing with at least one syringe assembly 12 and connecting the injector 10 to the proximal ends of the at least one syringe assembly 12 and to connect the plungers 26 to respective piston elements (not shown). The syringe ports 16 may be located in a top surface of the housing 14, and the housing 14 may be rotatable to direct the distal end of the at least one syringe assembly 12 in the vertical, horizontal, or downward facing direction. As will be described herein, the syringe assembly 12 includes at least one indicator, such as at least one indicator strip 34 (shown in FIG. 1B), at least one geometric pattern, or various combinations thereof, positioned on at least a portion of the outer circumferential surface of the syringe assembly 12, such as at least partially around the outer circumference at a proximal portion of the syringe assembly 12. The at least one indicator strip 34 may be embedded with or otherwise associated with identifying characteristics and other identifying information regarding the syringe assembly 12, including one or more of the syringe type, physical dimensions, flow characteristics, fluid contents, fluid source or type, manufacturer of the syringe, lot number, date of manufacture of the syringe, expiration of use date (i.e., the maximum shelf-life of the syringe), and similar syringe information, as described herein. In one aspect, the at least one indicator may comprise at least one conductive ink painted or printed onto at least a portion of the outer circumferential surface or inner circumferential surface of the syringe assembly 12 or onto at least a portion of an indicator strip 34 or other geometric patter on the outer circumferential surface of the syringe assembly 12. It is also contemplated that a plurality of indicator strips 34 and/or other geometric patterns may be positioned along one or more of a longitudinal axis and a latitudinal axis of the syringe assembly 12. In various aspects including more than one indicator strip 34 or geometric pattern, each indicator strip 34 or geometric pattern may contain at least a portion of the total information, as described herein, embedded within or otherwise associated with the indicator strip 34. In other aspects, each indicator strip 34 or geometric pattern may contain specific syringe information as described herein. In another aspect, each indicator strip 34 or geometric pattern may include the same syringe assembly 12 information to provide a redundant source of syringe assembly 12 information.

The at least one indicator strip 34 or geometric pattern may be read by at least one sensor 36 (shown in FIG. 1B), positioned on or recessed in at least a portion of the circumferential surface of the syringe ports 16 of the injector 10. In various aspects, the at least one sensor 36 may include, for example, at least one of a conductive elastomeric pad or strip 38 and a flex printed circuit board (PCB) 40. The conductive elastomeric pad may comprise one or a plurality of contact points within specific dimensions, such as length and/or width, along the circumferential surface of the syringe ports 16. For example, in one non-limiting aspect, the conductive elastomeric pad or strip 38 of the at least one sensor may have at least 15 contact points in a three-quarter inch (2 cm) width, which can create over 32,000 possible information codes pertaining to each contact point. In other aspects, the conductive elastomer pad or strip 38 of the at least one sensor 36 may have from 1 to 30 contact points within a 0.05 to 1.5 inch width within the circumferential surface of the syringe port 16. The information codes associated with the contact points may provide the syringe identifying information necessary to identify the syringe and/or syringe contents to the injector and/or operating system. The interaction between the at least one indicator strip 34 or geometric pattern and the at least one sensor 36 will be described in greater detail herein. In another aspect, the sensor 36 may be at least one metal spring contact sensor having one or more contact points within a specific width or length along the inner surface of the syringe ports 16.

A fluid path set (not shown) may be interfaced with the at least one syringe assembly 12, for example at a port or nozzle 24 of the distal end 22, supported by the powered injector 10 for delivering fluid from the syringe assembly 12 to a catheter, needle or other inserted fluid path (not shown) inserted into a patient at a vascular access site. For example, a flow of saline solution from one syringe assembly 12 and contrast from a second syringe assembly 12 may be regulated by a fluid control module (not shown) during an injection procedure. The fluid control module operates various valves and flow regulating structures, such as pistons or linear actuators, to regulate the delivery of the saline solution and contrast to the patient based on user selected injection parameters, such as injection flow rate, duration, total injection volume, and ratio of contrast media to saline, which may be programmed or otherwise entered into the injector operation system. A suitable multi-syringe injector is described in U.S. Patent Application Publication No. 2012/0123257, filed on Jan. 24, 2012, which is assigned to the assignee of the present application, the disclosure of which has been incorporated herein by reference hereinabove in its entirety. Other relevant multi-fluid delivery systems are found in U.S. Patent Application Publication No. 2004/0064041, filed on May 30, 2002, and in U.S. Patent Application Publication No. 2005/0113754, filed Nov. 25, 2003, both of which are assigned to the assignee of the present application, and the disclosures of which are incorporated herein by reference. The principles of this disclosure may be applied to fluid injectors that operate only a single syringe assembly 12 assembly or multiple syringe assemblies, such as, for example two or three syringe assemblies.

Figure 2:
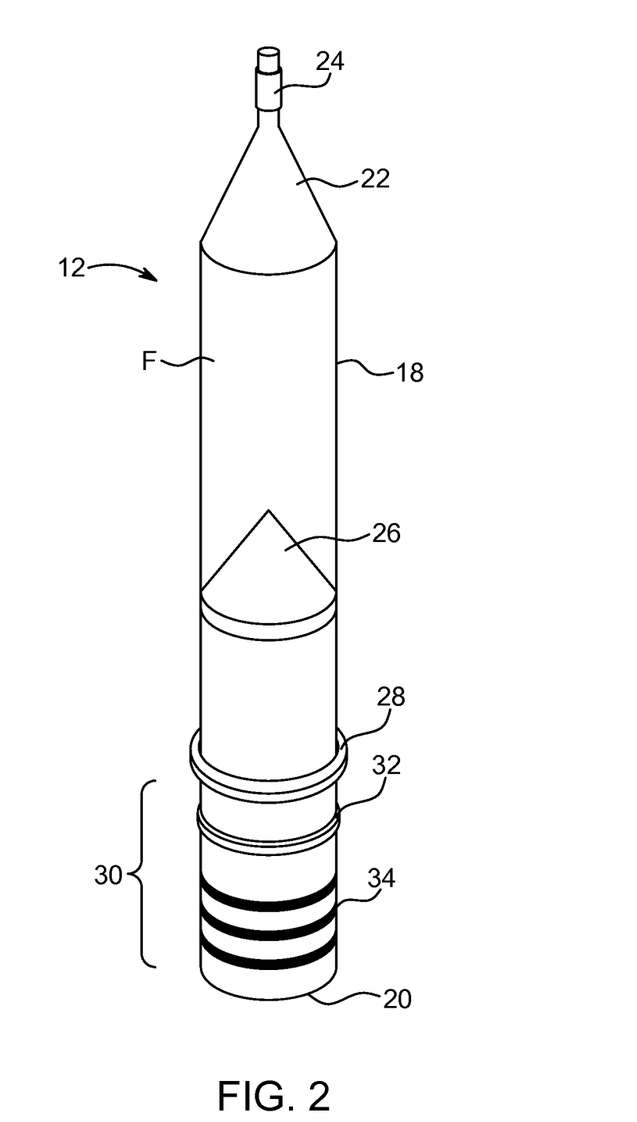
FIG. 2 is an elevational view of the syringe for use with the powered injector of FIG. 1A, according to an aspect of the disclosure.
Figure 3:
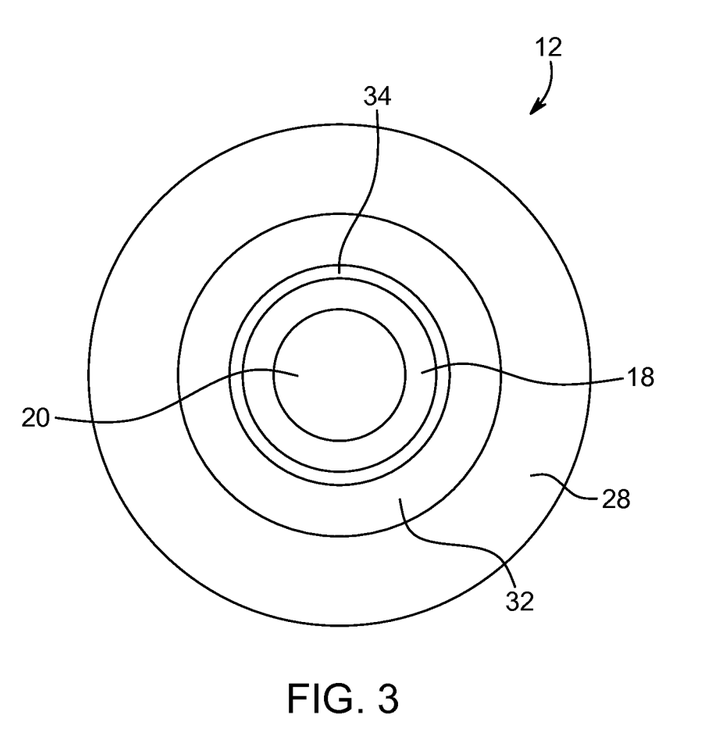
FIG. 3 is an end view of the syringe of FIG. 2.

Having described the structure and function of the powered injector 10, the at least one syringe assembly 12, containing a fluid F, for use with the injector 10, according to one aspect of the disclosure, will now be discussed in greater detail. With reference to FIG. 2, according to certain aspects, the syringe assembly 12 generally has a cylindrical syringe barrel 18 formed from glass or medical-grade plastic. The syringe barrel 18 may extend from an open proximal end 20 to a distal end 22 with a nozzle 24 extending therefrom. The open proximal end 20 may be sealed with an elastomeric plunger 26 within the syringe barrel 18. The plunger 26 may be reversibly slideable within the syringe barrel 18. The plunger 26 may form a liquid tight seal against the inner sidewall of the syringe barrel 18 as it is advanced or withdrawn therethrough through the action of a piston actuator associated with powered injector 10. According to certain aspects, an annular flange 28 may extend from the outer surface of the syringe barrel 18 at a position near the open proximal end 20 of the syringe barrel 18. When the syringe assembly 12 is interfaced with the injector 10 as shown in FIG. 1A, the flange, referred to herein as a drip flange 28, may rest against a distal end 17 of the syringe port 16 to prevent excess fluid expelled from the syringe assembly 12 from entering the syringe port 16 and fouling the interior workings of injector 10. The portion of the syringe barrel 18 near the open proximal end 20, for example between the drip flange 28 and the open proximal end 20 of the syringe assembly 12, referred to hereinafter as the insertion portion 30, is sized and adapted to be inserted in the syringe port 16 of the injector 10 (shown in FIG. 1B). Accordingly, in certain aspects, the insertion portion 30 of the syringe barrel 18 includes one or more locking structures, such as a locking flange 32, extending outward from the syringe barrel 18. The locking flange 32 or other locking structure may be adapted to form a locking engagement with corresponding protrusions or locking structures within the syringe port 16 of the injector 10 for releasably holding the syringe assembly 12 in the syringe port 16 while the injector 10 is in use. Alternatively, the insertion portion 30 may include various latches, locking mechanisms, or radially extending ribs for connection to corresponding portions of the syringe port 16. One aspect of a suitable syringe assembly 12 for use with the injector 10 depicted in FIGS. 1A and 1B may be found in U.S. Pat. No. 5,383,858, issued Jan. 24, 1995, and which is assigned to the assignee of the present application, the disclosure of which is incorporated herein by reference in its entirety. Other relevant syringe aspects may be found in U.S. Pat. No. 6,322,535, issued Nov. 27, 2001, and in U.S. Pat. No. 6,652,489, issued Nov. 25, 2003, each of which are assigned to the assignee of the present application, and the disclosures of which are both incorporated herein by reference.

With reference to FIGS. 1B-3, the syringe assembly 12, in one aspect, includes the at least one indicator strip 34 or geometric pattern positioned on at least a portion of an outer circumferential surface of the insertion portion 30. The indicator strips 34 or geometric patterns are configured to be located and read by at least one sensor in the injector 10, such as the at least one sensor 36 depicted in FIG. 1B. In an alternative aspect, the at least one indicator strip 34 may be embedded in the insertion portion 30 of the syringe assembly 12 during a molding or manufacturing process of the syringe assembly 12. In certain aspects, the at least one indicator strip 34 may have at least one conductive ink including conductive ink having coding for converting identifying information regarding the syringe assembly 12 that is inserted into the injector syringe ports 16. The at least one conductive ink may result in a printed object or circuitry that conducts electricity, for example over specific electrical circuits and pathways, corresponding to specific information regarding the syringe assembly 12. Different conductive inks, for example, having different electrical conductive and/or resistance properties may be used for different indicators of a plurality of indicators. The conductive ink may be printed or painted onto the insertion portion 30 of the syringe assembly 12 or on the outer surface of indicator strips 34 and may provide a conductive pathway for electrical signals that are read and interpreted by corresponding sensors on the interior surfaces of the at least one syringe port 16, for example, by conducting electricity from at least one first electrical contact of the sensor to at least one second electrical contact of the sensor. Contact between the sensor and the at least one first electrical contact of the sensor to at least one second electrical contact allows specific electrical circuits to form and conduct electricity through specific pathways corresponding to identifying information for the at least one syringe assembly 12. It is also contemplated that nearly transparent conductive inks could be used for covert or "invisible" coding on the insertion portion 30 of the syringe assembly 12. Various patterns for positioning the indicator strip 34 on the insertion portion 30 of the syringe assembly 12 are contemplated, including, equidistantly from one another, in small groups, variably-spaced from one another, or arranged in patterns around the circumference of the syringe body. However, the exact placement of the indicator strips 34 may not be critical as the at least one sensor 36, such as the conductive elastomeric pad or strip 38 or flex PCB 40, and the indicator strips 34 could have a finer resolution of detection. In other aspects, close association between the indicator strips 34 and the sensor 36 may be necessary for accurate reading and interpretation of the information on the conductive indicator strips 34.

With continued reference to FIGS. 1B-3, the one or more indicator strips 34 or geometric patterns may be embedded with or associated with identifying information about the syringe assembly 12 and/or the fluid F contained or to be contained therein. For example, the information may include the physical dimensions of the syringe assembly 12 (e.g., length and diameter, fluid volume, nozzle dimensions, etc.) or other information, such as, but not limited to, flow characteristics of a fluid stored in the at least one syringe assembly, a type of fluid stored in the at least one syringe assembly, manufacturer of the at least one syringe assembly, lot number, date of manufacture of the at least one syringe assembly, expiration of use date of the at least one syringe assembly, and combinations thereof. In addition, the one or more indicator strips 34 may include identifying information corresponding to physical parameter information for the syringe assembly 12, including date of manufacture, lot number and source, barrel/plunger friction characteristics, fluid pressure limitations and maximums, maximum or minimum flow rates, and fluid type. The physical parameter information and other identifying information about the syringe assembly 12 may be used to determine a preferred injection force, injection velocity, and appropriate power level for the linear actuator of the injector 10 and may also be used to determine if the syringe is appropriate for the indicated usage. Examples of types of relevant information that may be communicated or transmitted between a syringe assembly and an injector and/or operating system is discussed, for example, in U.S. Pat. No. 6,743,202, issued Jun. 1, 2004, and which is assigned to the assignee of the present application, the disclosure of which is incorporated herein by reference in its entirety.

According to certain aspects, the syringe assembly information may be directly embedded on the indicator strips 34 and/or the circuits formed therefrom when contacted with the sensor elements, and may be readable by a suitable electronic, optical, or imaging sensor for reading and extracting information from the indicator strips 34. Alternatively, relevant information on the syringe assembly 12 may not be embedded directly with the indicator strips 34 itself, but the indicator strips 34 may contain information that serves as a pointer directing the injector, a computer, processor, or controlling device to a location on a computer database, computer network, hospital information network, internet, or similar data storage location, by a wired or wireless connection, where specific information about the syringe assembly 12 is located and the information regarding information location may be read via the at least one sensor, such as sensor 36 upon interaction with the one or more indicator strips 34. Once located, the stored information can be downloaded to a computer accessory viewable by the injector operator or directly to the injector or injector operating system for preparing, adjusting, or modifying injection parameters.

The at least one indicator strip 34 may be provided in various shapes and spatial orientations around the outer circumferential surface of the insertion portion 30, depending on the size and/or shape of the insertion portion 30, injector 10, sensor 36 location, and/or syringe port 16. For example, the indicator strip 34 may be rectangular in shape or have another geometric shape or pattern. Alternatively, the indicator strips 34 may include a dotted line, with small or larger portions separated by spaces provided in between each portion. The dotted line may optionally surround at least a portion of the outer circumferential surface of the insertion portion 30. Further, the indicator strips 34 may have any appropriate shape, including a combination of a variety of shapes for separate portions of the indicator strip or adjacent or neighboring strips, for example, a circular, elliptical, or polygonal shape, such as triangular, quadrilateral, or other multisided shape. In certain cases, the shapes and their spatial orientation of the various features on the indicator strips 34 may also provide specific information regarding the syringe assembly parameters and identity when contacted by the sensor.

Figure 4:
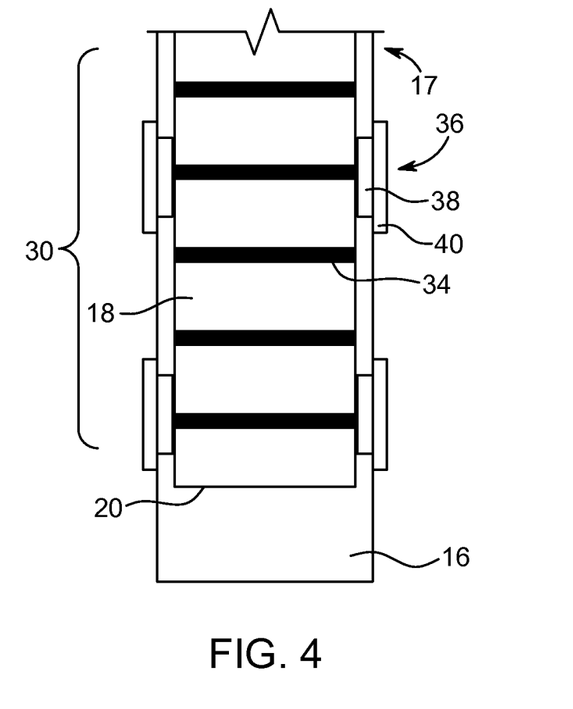
FIG. 4 is a side view of a syringe port of the injector of FIG. 1A with the syringe of FIG. 1A inserted therein.

As shown in FIGS. 1B and 4, the at least one sensor 36 of the injector 10 may be positioned on an inner surface of the syringe port 16. For example, according to certain aspects, at least one conductive elastomeric pad 38 may be attached to the flex PCB 40 and positioned on the inner surface of the syringe port 16. The at least one sensor 36 may extend around the entire circumferential surface of the syringe port 16 and may read the various portions and coding of the appropriately aligned indicator strip 34. Alternatively, the at least one sensor 36 may only extend around a portion of the circumferential surface of the syringe port 16. In one aspect, a single sensor 36 may be provided in the syringe port 16 for reading information from the indicator strips 34 of the syringe assembly 12. According to certain aspects, the single sensor 36 may read information from multiple indicator strips 34 as the insertion portion 30 is inserted into syringe port 16. In another aspect, at least two sensors 36 are provided in the syringe port 16 of the injector 10. In one aspect, one sensor 36 may be positioned above another sensor 36 along a longitudinal axis of the syringe port 16. By providing at least a second conductive elastomeric pad 38 and flex PCB 40, a redundant reading could be produced to ensure the correct information is being relayed from the indicator strips 34. Further, the second sensor 36 may be used to read a second coded pattern on a second or additional indicator strip 34 that cannot be read by the first sensor 36 from the first indicator strip 34. In this aspect, the first sensor 36 may be configured to read a first coded pattern relating to certain identifying information, e.g. syringe size, and the second sensor 36 may be configured to read a second coded pattern relating to different identifying information, e.g. syringe has been pre-filled with specific medical fluid F. According to other aspects, some but not all of the at least one indicator strip 34 on the syringe assembly 12 may contain relevant information regarding the syringe assembly and the contents and other indicator strips 34 on the syringe assembly 12 may contain no information and are not read by the at least one sensor 36.

Continuing with reference to FIG. 4, having described the structure of the syringe assembly 12, the at least one indicator strip 34 and the at least one sensor 36, the interaction between the syringe assembly 12 and syringe port 16 of the injector 10 will be further described. In one aspect, the at least one sensor 36 may be positioned on at least one inner surface of the syringe port 16. For example, at least one of sensor 36 may be positioned at a distal end 17 of the syringe port 16. In other aspects, at least one sensor 36 may be located more proximally within the syringe port 16. In certain aspects, the flex PCB 40 of the at least one sensor 36 may be recessed within or below the inner surface of the syringe port 16. The user may insert the insertion portion 30 of the syringe assembly 12 into the syringe port 16 of the injector 10, causing the at least one indicator 34 to contact the at least one sensor 36 when the syringe assembly is in the correct, locked position. In certain aspects, the user may rotate the syringe assembly 12 to establish direct contact between the indicator strips 34 and the sensor 36. In other aspects, the syringe assembly 12 may be inserted in any direction or in a direction determined by the construction of syringe port 16 and the at least one sensor 36 may be configured to contact and read information from the at least one indicator strip 34 regardless of the orientation at which the syringe assembly 12 is inserted. For example, the at least one sensor 36 may be located continuously or discontinuously around the complete circumference of syringe port 16 such that the sensor is configured to read the indicator strip 34 over the entire circumference of the insertion portion 30 of the syringe assembly 12. In still other embodiments, the syringe may self-orient itself during the insertion process to place the at least one indicator 34 and the at least one sensor 36 in the correct position to interact. Once direct electrical contact is established between the at least one conductive ink of the indicator strip 34 and the at least one sensor 36, syringe assembly information may be downloaded to or retrieved from the at least one indicator strip 34 by the at least one sensor 36. As the syringe assembly 12 is inserted into the at least one syringe port 16, one of the indicator strips 34 may contact the sensor 36 and, in particular, the conductive elastomeric pad 38, thereby causing the conductive ink of the indicator strip 34 to conduct electricity from at least one first electrical contact on the sensor to at least one second electrical contact on the sensor. The conducted electricity is directed to the flex PCB 40, which interprets the conducted electricity to determine specific information regarding the syringe assembly 12, for example, based on features of the circuit formed by the electrical contact. The conductive ink of the indicator strip 34 may contact one or more contact points of the elastomeric pad 38, thereby causing the conductive ink to conduct electricity.

Figure 5:
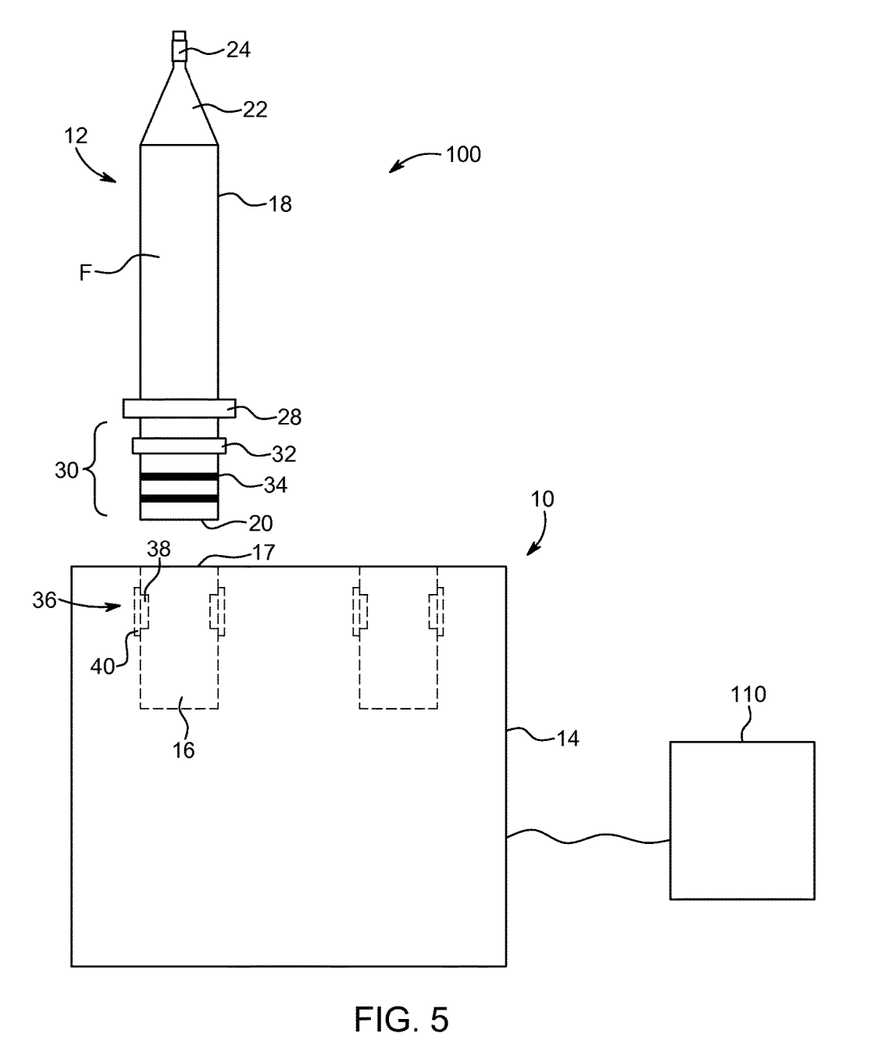
FIG. 5 is a schematic view of a fluid delivery system including a syringe and a powered fluid injector according to an aspect of the disclosure.

With reference to FIG. 5, one aspect of an injection system 100 including the at least one syringe assembly 12, the attached at least one indicator strip 34, injector 10, and the at least one sensor 36, is illustrated. In use, an operator inserts the proximal end 20 of the at least one syringe assembly 12 into the at least one syringe port 16. Other aspects may include two syringe assemblies and two corresponding syringe ports on the injector 10. The operator may be required to exert some force against the syringe assembly 12 so that the locking flange 32 or other locking mechanism of the syringe assembly 12 engages with the corresponding locking structures (not shown) of the syringe port 16 until the insertion portion 30 of the syringe barrel 18 is entirely inserted into and engaged with syringe port 16. Once the syringe assembly 12 is inserted in the syringe port 16, the operator may optionally twist and rotate the syringe assembly 12 relative to the syringe port 16 until the syringe assembly 12 is in the "home" or "ready-to-use" position or the syringe assembly 12 may self-orient itself during insertion into syringe port 16. In other aspects, the injection head and syringe port 16 may include a spring loaded or other locking mechanism which automatically rotates the syringe assembly 12 into the "ready-to-use" position, thereby reducing opportunity for operator error during the insertion process. Twisting the syringe assembly 12, either manually or automatically, may bring the at least one indicator strip 34 located on the outer surface of the barrel 18 into contact with the at least one sensor 36 and, more specifically, the at least one conductive elastomeric pad 38 of the at least one sensor 36. In still other aspects where the at least one sensor 36 may read the entire outer circumferential surface of the syringe assembly 12, the syringe assembly 12 may not need a specific angle of rotation or orientation to place the at least one indicator strip 34 and at least one sensor 36 in the "ready-to-use" position. When the at least one indicator strip 34 and the at least one sensor 36 are correctly aligned with respect to one another, the injector 10 may be configured to read and send the information from the at least one indicator strip 34 to one or more computer accessory or processor 110, such as a computer processor, a computer terminal, injector software, hospital information network, or portable electronic device, such as a cell phone, computer tablet, or laptop computer, by a wired or wireless connection, associated with the injector 10, for example to provide a visual or audible alert regarding the identifying information about the syringe assembly 12. This information may be used by the injector 10, for example, to prepare, modify, or adapt the injector settings based on the identifying information prior to initiating the injection process. Similarly, the injector 10 may be configured to warn an operator or cancel or prevent the injection procedure if the loaded syringe assembly 12 or fluid F contained therein is inappropriate for the procedure to be performed or if the syringe assembly 12 is not configured for the specific injector. Assuming that the syringe assembly 12 and fluid are correct, the injector 10 may automatically begin the injection procedure, optionally using a portion of the information contained in the at least one indicator. Alternatively, the operator may be required to initiate the injection procedures by an actuation activity, such as pressing a start button. Once the injection is actuated, the linear actuator of the injector 10 contacts and engages the proximal end of the plunger 26 disposed within the syringe barrel 18, for example to initiate filling of an empty syringe or begin injection for a prefilled syringe. Once the at least one syringe 12 is filled with fluid, movement of the plunger 26 in a proximal direction may draw in fluid into the syringe assembly 12 via negative pressure. Movement of the plunger 26 in the distal direction expels fluid contained within the syringe assembly 12 from the nozzle 24, thereby injecting fluid through a tubing assembly into the patient through any known injection structure, such as an IV tube or needle accessory.

Although the disclosure has been described in detail for the purpose of illustration based on what is currently considered to be the most practical and preferred aspects, it is to be understood that such detail is solely for that purpose and that the disclosure is not limited to the disclose aspects, but, on the contrary, is intended to cover modifications and equivalent arrangements. For example, it is to be understood that the present disclosure contemplates that, to the extent possible, one or more features of any aspect can be combined with one or more features of any other aspect.

What is claimed is:

1. A system for identifying information regarding a syringe assembly used with a fluid injector, the system comprising:
    at least one syringe assembly having a barrel extending from a distal end to an open proximal end;
    at least one indicator provided on at least a portion of an outer circumferential surface of the barrel;
    a fluid injector having at least one syringe port adapted to receive the at least one syringe assembly; and
    at least one sensor provided on or within at least a portion of the at least one syringe port,
    wherein the at least one sensor comprises a conductive elastomeric pad that contacts the at least one indicator and a flex printed circuit board that interprets the information regarding the at least one syringe assembly, and wherein the at least one indicator conducts electricity corresponding to the information regarding the at least one syringe assembly, which is identified by the at least one sensor.

2. The system as claimed in claim 1, wherein the at least one indicator comprises at least one conductive ink.

3. The system as claimed in claim 1, wherein the information regarding the at least one syringe assembly comprises at least one of a type of the at least one syringe assembly, physical dimensions of the at least one syringe assembly, flow characteristics of fluid stored in the at least one syringe assembly, a type of fluid stored in the at least one syringe assembly, a manufacturer of the at least one syringe assembly, a lot number of the at least one syringe assembly, a date of manufacture of the at least one syringe assembly, an expiration of use date of the at least one syringe assembly, and combinations thereof.

4. The system as claimed in claim 1, wherein, upon contacting the conductive elastomeric pad, the at least one indicator conducts electricity from at least one first electrical contact to at least one second electrical contact that corresponds to the information regarding the at least one syringe assembly and that is interpreted by the flex printed circuit board.

5. The system as claimed in claim 1, further comprising a computer accessory in communication with the at least one sensor.

6. The system as claimed in claim 1, wherein the at least one indicator extends entirely around the outer circumferential surface of the barrel.

7. The system as claimed in claim 1, wherein the at least one indicator is formed as at least one strip, at least one geometric pattern, or combination thereof.

8. The system as claimed in claim 1, wherein the at least one indicator is formed on a proximal portion of the syringe barrel.

9. The system as claimed in claim 1, wherein the at least one sensor extends around at least a portion of a circumferential surface of the at least one syringe port.

10. The system as claimed in claim 1, wherein the at least one sensor comprises at least two sensors, and
wherein the at least two sensors are spaced apart from one another along at least one of a longitudinal axis and a lateral axis of the at least one syringe port.

11. The system as claimed in claim 1, wherein the at least one indicator is detectable by the at least one sensor when the at least one syringe assembly is engaged within the at least one syringe port.

12. The system as claimed in claim 1, wherein the at least one indicator comprises a plurality of indicators, and
wherein each of the plurality of indicators corresponds to different information regarding the at least one syringe assembly.

13. A syringe assembly, comprising:
a barrel extending from a distal end to an open proximal end, and
at least one indicator comprising at least one conductive ink provided on at least a portion of an outer circumferential surface of the barrel,
wherein the at least one indicator is configured to conduct electricity from at least one first electrical contact to at last one second electrical contact that corresponds to information regarding the at least one syringe assembly when contacted by at least one sensor provided on or within at least a portion of at least one syringe port of a fluid injector, and
wherein the at least one sensor comprises a conductive elastomeric pad that contacts the at least one indicator and a flex printed circuit board that interprets the information regarding the at least one syringe assembly.

14. The syringe assembly as claimed in claim 13, wherein the at least one indicator corresponds to identifying information about the syringe assembly, and
wherein the identifying information comprises at least one of a type of the at least one syringe assembly, physical dimensions of the at least one syringe assembly, flow characteristics of fluid stored in the at least one syringe assembly, a type of fluid stored in the at least one syringe assembly, a manufacturer of the at least one syringe assembly, a lot number of the at least one syringe assembly, a date of manufacture of the at least one syringe assembly, an expiration of use date of the at least one syringe assembly, and combinations thereof.

15. The syringe assembly as claimed in claim 13, wherein the at least one indicator extends entirely around the outer circumferential surface of the barrel.

16. The syringe assembly as claimed in claim 13, wherein the at least one indicator is formed as at least one strip, at least one geometric pattern, or combination thereof.

17. The syringe assembly as claimed in claim 13, wherein the at least one indicator is provided on a proximal portion of the barrel.

18. The syringe assembly as claimed in claim 13, wherein the at least one indicator comprises a plurality of indicators, and
wherein each of the plurality of indicators corresponds to different identifying information regarding the syringe assembly.

19. A method for reading identifying information regarding a syringe assembly provided within a fluid injector, the method comprising:
providing a syringe assembly having at least one indicator comprising at least one conductive ink provided on at least a portion of a barrel of the syringe assembly;
inserting the syringe assembly into a syringe port of a fluid injector;
contacting the at least one indicator against a conductive elastomeric pad of at least one sensor provided within at least a portion of the syringe port, thereby causing the at least one indicator to conduct electricity from at least one first electrical contact to at least one second electrical contact; and
receiving identifying and interpreting information by a flex printed circuit board regarding the syringe assembly based on the electricity conducted by the at least one indicator.

* * * * *